US00PP09081P

United States Patent [19]

Button et al.

[11] Patent Number: Plant 9,081

[45] Date of Patent: Mar. 14, 1995

[54] AGLAONEMA PLANT NAMED PAINTED PRINCESS

[75] Inventors: Richard J. Button, Miami; Ann E. Lamb, Lake Placid, both of Fla.

[73] Assignee: Sunshine Foliage World, Zolfo Springs, Fla.

[21] Appl. No.: 223,856

[22] Filed: Apr. 6, 1994

[51] Int. Cl.[6] ..... A01H 5/00

[52] U.S. Cl. ..... Plt./88.1

[58] Field of Search ..... Plt. 88.1

*Primary Examiner*—Howard J. Locker

*Attorney, Agent, or Firm*—Foley & Lardner

[57] ABSTRACT

An Aglaonema plant named Painted Princess characterized by its abundantly marked silver-green on dark green tricolor, sharply tapered leaves, rapid growth, and tolerance to cold.

2 Drawing Sheets

The present invention comprises a new and distinct cultivar of Aglaonema, botanically known as *Aglaonema hybrida,* and referred to by the cultivar named Painted Princess.

The new cultivar is a product of a planned breeding program carried out by the inventor Richard J. Button in Miami, Fla. 33134. The new cultivar is a product of a cross of unknown parentage.

The first act of asexual propagation of Painted Princess occurred when offshoots and tissue culture of plants of the new cultivar were taken in Palmdale, Fla. under the supervision of inventor Anne E. Lamb. That and subsequent asexual reproduction both by tissue culture and offshoots have clearly established that the combination of characteristics of the new cultivar disclosed herein are firmly fixed and are retained through successive generations of asexual reproduction.

The following observations, measurements and values describe plants grown in Zolfo Springs, Fla. under shadehouse conditions which closely approximate those generally used in horticultural practice.

The following traits have been repeatedly observed to be characteristics which in combination distinguish Painted Princess from other Aglaonema of the same general type, for example, the well known cultivar Silver Queen.

1. The leaves of Painted Princess are longer than the leaves of Silver Queen, and are distinctly tapered to a point.

2. The leaves of Painted Princess are abundantly marked with three shades of green.

3. Plants of Painted Princess grow rapidly, attaining marketable size in approximately 20% less time than Silver Queen.

4. Plants of Painted Princess, unlike Silver Queen, show little or no foliar damage when exposed to low temperatures of 40 F for approximately 3 hours.

All color references are measured against The Royal Horticultural Society Colour Chart. Colors are approximate as color depends on horticultural practices such as light level and fertilization rate, among others, without, however, any variance in genotype.

In the drawings, the color photograph on Sheet 1 is a top perspective view of Painted Princess. The color photocopy comprising Sheet 2 shows the leaf color pattern in more detail, illustrating in greater detail the leaf coloration pattern on the adaxial surface The photograph on sheet 1 is of a plant of Painted Princess in a 26 cm pot approximately 69 weeks after planting a single 4 leaf cutting and grown under appropriate growing conditions. Colors are as accurate as possible with color illustrations of this type.

Origin: Seedling selected from a cross of unknown parentage.

Classification: *Aglaconema hybrida,* cv, Painted Princess.

Propagation: Asexual propagation either by division or tissue culture.

Plant: A 4 leaf cutting grown in a 26 cm pot for 69 weeks under appropriate growing conditions attains a height of approximately 14 cm. to 18 cm., measured from the soil surface to the junction of the petioles of the last two (2) unrolled leaves, and is approximately 75 cm to 80 cm. in width.

Stem:

*Growth pattern.*—The stem is erect in growth and approximately 1.4 cm to 1.6 cm in diameter five (5) cm above the soil surface. Internode distance is approximately 1.3 cm to 1.8 cm 3 cm above the soil.

*Color.*—Immature: 145 A-B. Mature: Where exposed to direct light, darker and greener than 137 A.

Petiole: The following information is based on the 4th expanded leaf from the apex.

*Growth pattern.*—The petiole has fleshy edges extending from the midrib that will be referred to as wings. The wings are approximately 4 mm to 9 mm wide one-half the distance from the petiole base to the wing apex. The wings extend from the base of the petiole to within approximately 6.2 cm to 7.1 cm of the base of the leaf. The apex of the wings is rounded, and often dried and brown. The petiole follows the stem axis but diverges from the axis approximately 13 cm to 14.5 cm from the leaf base, forming a horizontal distance from the edge of the stem to the leaf base of approximately 5.0 cm to 6.5 cm.

*Dimensions.*—The petiole is straight from its base to the base of the leaf. The petiole is approximately 6 mm in diameter one-half the distance between the top of the wing and the base of the leaf. The petiole is approximately 16 cm to 18.5 cm in length.

*Color.*—The petiole color is greener than, but closest to, 137 A, and often streaked with 137 C. The petiole wings are closest to 137 A but slightly darker and greener.

Leaf:

*Growth pattern.*—The leaf is ovate with an acute apex and a truncate to cordate base. The margin is entire. The leaf is asymmetric with the side of the leaf unrolling first having less surface area than the side unrolling last. The leaf is oriented parallel to the stem axis at the time of full unrolling, changing to approximately 35 degrees to the stem axis as more leaves unroll above it. The midrib is straight, or curved downward. The leaf blade is flat or somewhat wavy from the midrib to the margin, and often wavy along the margin.

*Dimensions.*—For the pot size and growing time indicated, the largest leaves are approximately 25 cm to 28 cm long and approximately 7 cm to 8.9 cm wide. Average sized leaves are approximately 22 cm to 24 cm long and approximately 6.5 cm to 7 cm wide. The leaf is moderately thick.

*Midrib.*—The midrib is thick and prominent, recessed on the upper leaf surface and protruding from the lower surface. The color of the midrib on the upper surface is greener than but closest to 139 A mottled with 189 A on new leaves, and darker and greener than but closest to 139 A mottled with 189 A on mature leaves. The color of the midrib on the abaxial is 137 C on new and mature leaves.

*Primary veins.*—The primary veins are sunken into the upper surface and protrude slightly from the underside. The primary veins on the upper surface are the same color as the tissue surrounding them. The primary veins are 137 A lightly mottled with 147 D on the under surface.

*Color and pattern.*—The upper leaf surfaces are abundantly marked with three shades of green. Dark green markings are located along approximately one half of the midrib and often along the leaf margins. Large prominent silver-green markings occupy much of the central leaf surface. There are irregular blotches of a third shade of silver-green which radiate out along the primary veins from the midrib to near the leaf margin. Unusual mosaic blotches made up of tiny specks of all three shades of green occur along the leaf blade near the midrib.

*Colors.*—Dark green markings: New leaves and mature leaves, upper surface, are darker and greener than, but closest to 139 A. Prominent silver-green markings, upper surface: New leaf: 189 A. Mature leaf: 189 A. Secondary silver-green markings, upper surface: New leaf: Greener than but closest to 191 A. Mature leaf: 191 A. The under leaf surfaces are 137 C on new and 137 B on mature leaves.

*Axillary breaks.*—There are approximately 14 axillary breaks with at least one leaf expanded. Leaves will show true color and pattern by the first leaf.

*Inflorescence.*—Typical of Aglaonema and does not have commercial significance.

Roots: Thick white roots with fine laterals.

General observation: Aglaonema 'Painted Princess' has sharply tapered leaves abundantly marked with two shades of silver-green on a dark green background. The plants grow rapidly, and tolerate low temperatures to 40 F for at least three hours without notable foliar damage. These combined characteristics make Painted Princess a unique new cultivar.

We claim:

1. A new and distinct cultivar of Aglaonema plant named Painted Princess, as illustrated and described.

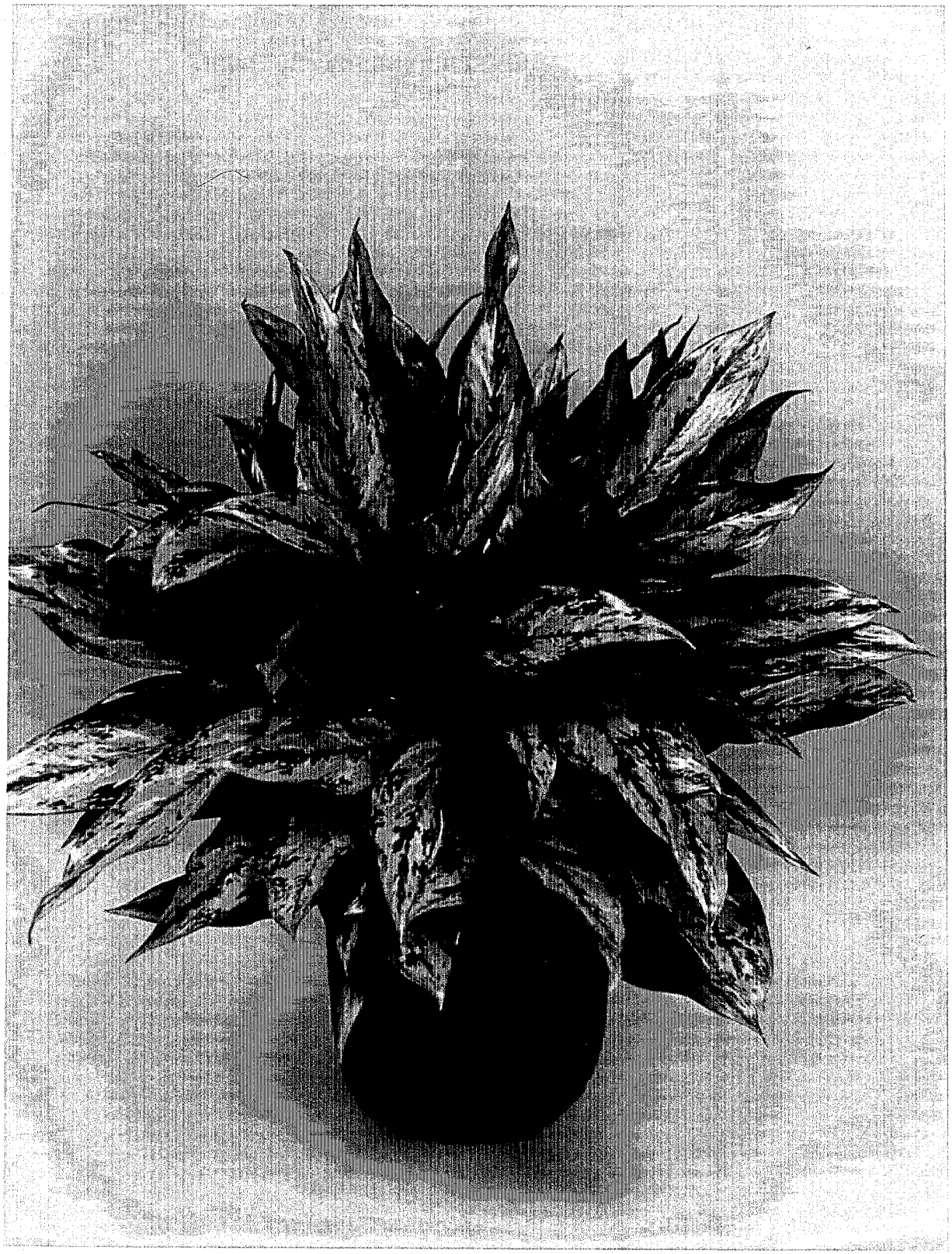

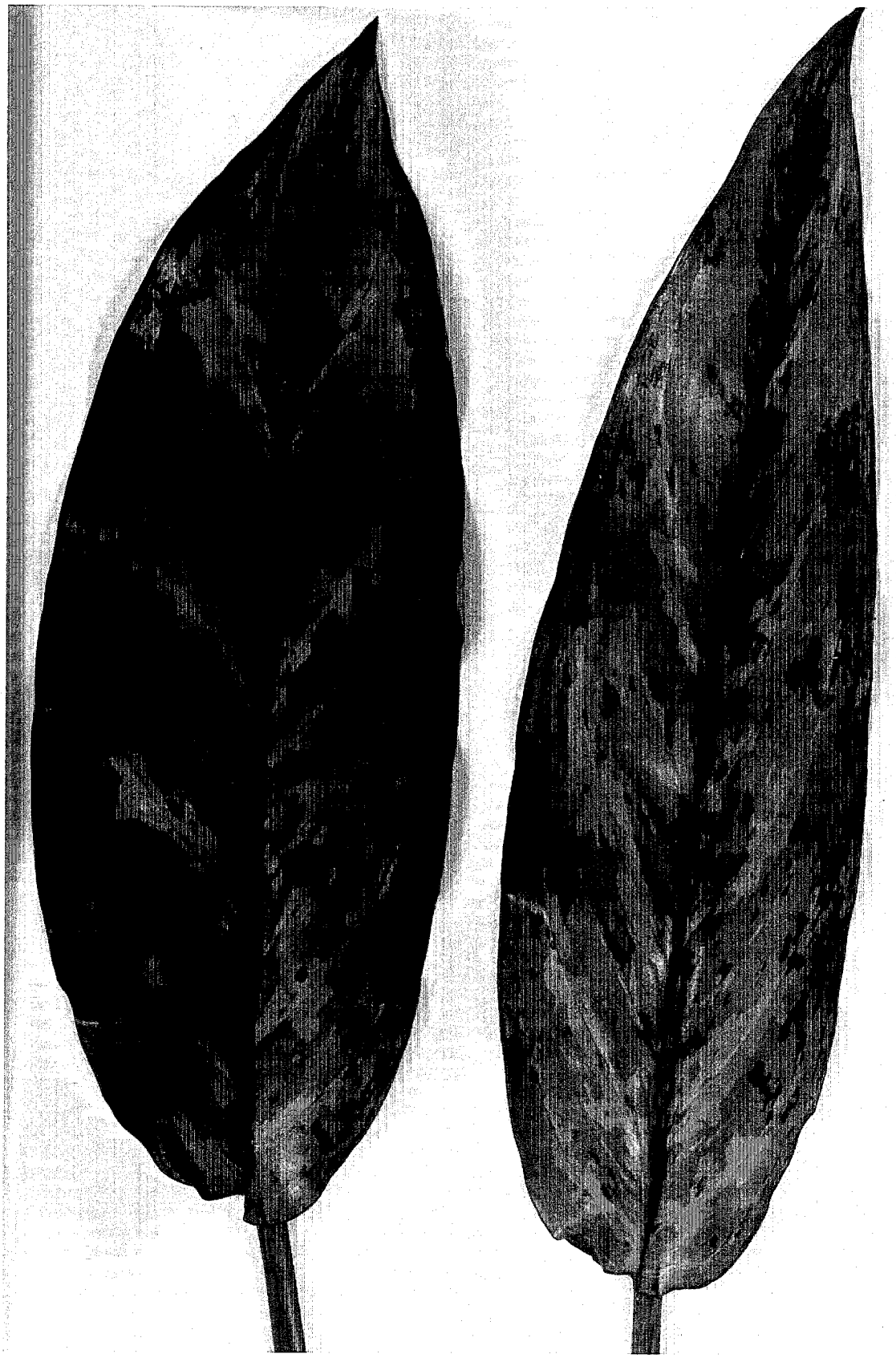

* * * * *